(12) United States Patent
Margaritova et al.

(10) Patent No.: US 10,527,639 B2
(45) Date of Patent: Jan. 7, 2020

(54) DETECTION APPARATUS AND METHOD FOR MEASURING THE EFFECT OF RADIATION ON BIOLOGICAL OBJECTS

(71) Applicant: SENSONICA LIMITED, Nicosia (CY)

(72) Inventors: Oxana Margaritova, Toscolano-Maderno (IT); Andrey Khodkin, Moscow (RU)

(73) Assignee: SENSONICA LIMITED, Nicosia (CY)

( * ) Notice: Subject to any disclaimer, the term of this patent is extended or adjusted under 35 U.S.C. 154(b) by 0 days.

(21) Appl. No.: 16/195,357

(22) Filed: Nov. 19, 2018

(65) Prior Publication Data
US 2019/0154844 A1    May 23, 2019

(30) Foreign Application Priority Data
Nov. 19, 2017 (EP) .................................. 17202468

(51) Int. Cl.
| | |
|---|---|
| *G01T 1/11* | (2006.01) |
| *G01N 37/00* | (2006.01) |
| *G01T 1/20* | (2006.01) |
| *G01N 21/71* | (2006.01) |
| *G01T 1/208* | (2006.01) |
| *G01T 3/06* | (2006.01) |
| *G01N 21/64* | (2006.01) |
| *G21F 3/00* | (2006.01) |
| *G01C 1/02* | (2006.01) |
| *G01S 3/04* | (2006.01) |
| *G01T 1/29* | (2006.01) |
| *G01S 3/782* | (2006.01) |

(52) U.S. Cl.
CPC ............ *G01N 37/005* (2013.01); *G01C 1/02* (2013.01); *G01N 21/64* (2013.01); *G01N 21/71* (2013.01); *G01S 3/043* (2013.01); *G01S 3/782* (2013.01); *G01T 1/11* (2013.01); *G01T 1/20* (2013.01); *G01T 1/208* (2013.01); *G01T 1/2018* (2013.01); *G01T 1/2907* (2013.01); *G01T 3/06* (2013.01); *G21F 3/00* (2013.01)

(58) Field of Classification Search
CPC ................................. G01T 1/11; G01N 21/71
USPC ........................................................ 250/362
See application file for complete search history.

(56) References Cited

U.S. PATENT DOCUMENTS

| | | | |
|---|---|---|---|
| 3,539,806 A | 11/1970 | Humphrey | |
| 5,658,673 A | 8/1997 | Holwitt et al. | |

(Continued)

FOREIGN PATENT DOCUMENTS

| | | |
|---|---|---|
| GB | 2440588 | 2/2008 |
| WO | 2015038861 | 3/2015 |

OTHER PUBLICATIONS

Dias et al., "Photo physics of thermally activated delayed fluorescence molecules," Methods and Applications in Fluorescence, vol. 5, No. 1, 012001, Mar. 9, 2017, 26 pages.

(Continued)

*Primary Examiner* — David P Porta
*Assistant Examiner* — Gisselle Gutierrez
(74) *Attorney, Agent, or Firm* — Hanley, Flight & Zimmerman, LLC.

(57) ABSTRACT

Radiation detection arrangement and method for measuring the effect of radiation on a biological object using (thermally activated delayed fluorescence) TADF material based detection of radiation.

14 Claims, 7 Drawing Sheets

(56) References Cited

U.S. PATENT DOCUMENTS

| | | | |
|---|---|---|---|
| 2014/0034930 A1* | 2/2014 | Seo | H01L 51/5016 257/40 |
| 2015/0076360 A1* | 3/2015 | Menge | G01T 3/06 250/390.11 |
| 2016/0172605 A1* | 6/2016 | Seo | H01L 51/5016 257/40 |
| 2016/0178542 A1 | 6/2016 | Lingren et al. | |
| 2016/0197282 A1* | 7/2016 | Tanimoto | H01L 51/0057 257/40 |
| 2016/0268516 A1* | 9/2016 | Tanaka | H01L 51/0072 |
| 2017/0133617 A1* | 5/2017 | Seo | H01L 51/5016 |
| 2017/0162817 A1* | 6/2017 | Ogiwara | H01L 51/504 |
| 2017/0229670 A1* | 8/2017 | Laitar | H01L 51/0091 |
| 2017/0256733 A1* | 9/2017 | Tsukamoto | H01L 51/50 |
| 2017/0271597 A1* | 9/2017 | Miyata | C07D 413/14 |
| 2018/0226600 A1* | 8/2018 | Seo | H01L 51/5016 |
| 2018/0323396 A1* | 11/2018 | Tsukamoto | H01L 51/50 |
| 2018/0337360 A1* | 11/2018 | Huang | H01L 51/5008 |
| 2019/0067615 A1* | 2/2019 | Seo | H01L 51/5016 |
| 2019/0271779 A1 | 9/2019 | Margaritova et al. | |

OTHER PUBLICATIONS

European Patent Office, "Extended European Search Report," issued in connection with European Patent Application No. 17202468.9, dated Jun. 7, 2018, 9 pages.

European Patent Office, "Examination Report," issued in connection with European Patent Application No. 17202468.9, dated Apr. 9, 2019, 10 pages.

Tibor Jacob Hajagos, "Plastic Scintillators for Pulse Shape Discrimination of Particle Types in Radiation Detection," Jun. 6, 2017, XP855572429, retrieved from the Internet: URL:https://search.proquest.com/docview/1916898229?pq-origsite=gscholar, 150 pages.

European Patent Office, "Extended European Search Report," issued in connection with European Patent Application No. 18000910.2, dated Apr. 17, 2019, 15 pages.

European Patent Office, "Extended European Search Report," issued in connection with European Patent Application No. 18000909.4, dated Feb. 1, 2019, 14 pages.

William T. Joines et al., "Electromagnetic Emission From Humans During Focused Intent," The Journal of Parapsychology, Oct. 1, 2012, XP55574740, retrieved from the Internet: URL:http://www.rhine.org/images/jp/v76Fall2012/dJPF2012Joines.pdf, 20 pages.

Beverly Rubik et al., "Effects of Intention, Energy Healing, and Mind-Body States on Biophoton Emission Introduction," The Journal of Natural and Social Philosophy, Apr. 2, 2017, XP55574742, retrieved from the Internet:URL:https://pdfs.semanticscholar.org/706b/86f2b35fb0100105431e3edce06d019664f9.pdf, 22 pages.

Nobuhiro Yanai et al., "New Triplet Sensitization Routes for Photon Upconversion: Thermally Activated Delayed Fluorescence Molecules, Inorganic Nanocrystals, and Singlet-to-Triplet Absorption," Accounts of Chemical Research., vol. 50, No. 10, Sep. 20, 2017, pp. 2487-2495, XP55574763, 10 pages.

J.L. Kiel, "Molecular Dosimetry", Radio Frequency Radiation Dosimetry and Its Relationship to the Biological Effects of Electromagnetic Fields, Springer Netherlands, Dordrecht, pp. 227-237, Jan. 1, 2000, XP809510393, retrieved from the Internet: URL:https://link.springer.com/chapter/10.1007/978-94-011-4191-8_25, 12 pages.

Mehmet Yuksel et al., "Dosimetric Characteristics of Anhydrous Borax," Sep. 2-4, 2015, XP55540889, Retrieved from the Internet:URL:https://www.researchgate.net/publication/282505033_Dosimetric_Characteristics_of_Anhydrous_Borax, 6 pages.

United States Patent and Trademark Office, Non-final Office Action, issued in connection with U.S. Appl. No. 16/195,326, dated Oct. 18, 2019, 14 pages.

* cited by examiner

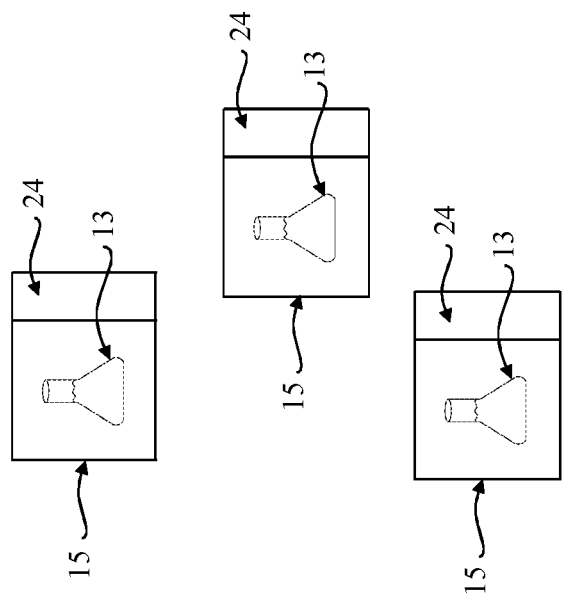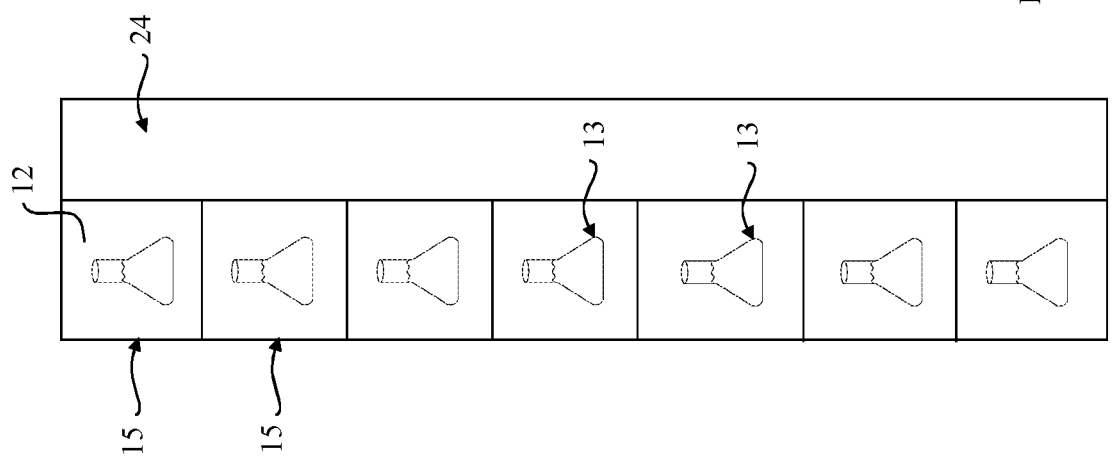

DETECTION APPARATUS AND METHOD FOR MEASURING THE EFFECT OF RADIATION ON BIOLOGICAL OBJECTS

FIELD OF THE INVENTION

The present invention relates, generally, to the field of detection of radiation and biology, more particularly, to measuring the effect of radiation on biological objects using TADF (thermally activated delayed fluorescence) material based detection of radiation.

BACKGROUND OF THE INVENTION

Biological and/or living objects on Earth, such as plants, animals, humans or the like are exposed to cosmic and/or terrestrial radiation or anthropogenic emissions. The impact of these radiations affects the natural course of biophysical reactions, including the probability of induced DNA mutations, the transmission of chemical and electrical signals by cells, and the viability of the biological organism as a whole. To this end, appropriate radiation detectors are used to measure potentially hazardous emissions.

However, conventional detectors used for example in industrial ecology are only able to measure or determine a limited range of radiation and the entire spectrum of potentially hazardous emissions cannot be measured or determined.

For example, dosimeters are limited by the measurement of ionizing radiation of a particular energy.

Conventional methods to estimate the effect of radiation on biological objects are carried out by accessing their viability, e.g. relying on heart rate variability. Accordingly, such methods may be influenced by additional factors affecting the measurements.

OBJECTION OF THE INVENTION

An object of the present invention is to provide a solution for measuring and analyzing the effect or impact of radiation on biological objects.

SUMMARY OF THE INVENTION

To solve the above object, the present invention provides subject-matter according to the accompanying independent claims, wherein variations, embodiments and examples thereof are defined in accompanying dependent claims.

More particularly, the present invention provides a detection arrangement for measuring the effect of radiation on biological objects, the arrangement comprising:
  a detection layer comprising thermally activated delayed fluorescence TADF material, the thermally activated delayed fluorescence TADF material having an excitation frequency range and, exhibiting upon excitation with radiation in the excitation frequency range, a thermally activated delayed fluorescence TADF emission, wherein
  the TADF material having a TADF emission without exposure to external radiation and exhibiting a deviation in the TADF emission with exposure to external radiation.

The detection layer of the arrangement for measuring the effect of radiation on biological objects of the present invention may be sub-divided into at least two channels,
  wherein each channel comprises the same TADF material or
    at least one channel, a plurality of channels or each channel comprises a different TADF material,
  wherein the components of the TADF material are selected and/or mixed in order to create a suitable TADF material
    such that the properties of the resulting TADF material are physically, biologically and/or chemically substantially identical to the properties of the biological object and/or
    such that the activation energy of the resulting TADF material is substantially identical to the activation energy of biochemical reactions of the biological object; wherein
      the biological object is arranged in the vicinity of the radiation detection arrangement and
    is being exposed to substantially the same external radiation as the radiation detection arrangement;
wherein the detection arrangement is further comprising:
  a computing device,
  an excitation radiation source device adapted to emit excitation radiation in the excitation frequency range, wherein
  the excitation radiation causes TADF emission(s) of one or more of the TADF material(s), wherein
  each of the one or more TADF emission(s) having a brightness B that is depending on the composition of the TADF material and/or on the temperature T comprised in the one or more channels of the detection layer,
  a radiation detector device communicatively coupled with the computing device, the radiation detector device being adapted to detect TADF emission from the one or more channels and provide respective detection data to the computing device,
  wherein the computing device is being adapted to:
    compute detection data from the radiation detector device to determine a TADF emission without exposure to external radiation and a deviation of the TADF emission with exposure to radiation,
    determine a brightness B of one or more TADF emission(s) in the detection layer and/or one or more channels(s) and
    calculate a deviation of the brightness B of a TADF emission without exposure to external radiation and a brightness B of TADF emission with exposure to external radiation,
    determine and/or derive, on the basis of the deviation of the brightness B and/or the temperature T of one or more TADF material(s) comprised in the detection layer and/or one or more channels, the effect of the external radiation on the biological object.

The detection layer and/or one or more channel(s) of the detection arrangement may be at least one of
  planar,
  provided in a coating material,
  shaped as a part of a sphere,
  shaped as a hollow or solid sphere,
  shaped as a polyhedron.

The detector device may comprise at least one of
  a photo detector,
  a discrete radiation detector,
  a radiation detector array including at least two detector elements,
  electro-optical transducer,
  image intensifier tube, vacuum tube,
CMOS chip
a CCD chip.

The detection arrangement may comprise at least two radiation detector devices, wherein the detection layer is arranged between the at least two radiation detector devices.

The detection arrangement may comprise a control device for controlling the operation of the excitation radiation source device, wherein the control device is adapted to operate the excitation radiation source device in a constant emission mode and/or a variable/modifiable emission mode, comprising pulsed and/or periodical emission mode.

The computing device may be able to compute detection data from the radiation detector device during and/or following radiation emission from the excitation radiation source device and/or
   an optical system being arranged between the detection layer and/or one or more channel(s) and one or more of the radiation detector device.

The detection arrangement of one of the preceding claims may comprise a housing accommodating the components of the detection arrangement.

The housing may have shielding properties for shielding of at least one of:
   electro-magnetic radiation;
   X-ray radiation;
   ultraviolet radiation;
   Gamma radiation;
   corpuscular radiation, comprising alpha radiation, beta radiation, neutrons and/or protons.

The detection arrangement may comprise at least one temperature sensing device for sensing temperature of at least one of
   the detection layer,
   the one or more channel(s)
   one or more TADF material(s),
   the excitation radiation source device,
   the radiation detector device,
   the housing,
   the optical system,
   the computing device.

The detection arrangement or at least one or more parts thereof may be placed/arranged in a temperature-controlled environment.

For example, it is envisaged to use a passive temperature-controlled environment, where the radiation detection arrangement or one or more parts thereof may be arranged in a box, container, housing and the like having thermal characteristics (e.g. walls with high thermal resistance) that maintain a temperature in its interior at least for some period of time. Examples for a passive temperature-controlled environment include a Dewar flask/container.

Further, it is also envisaged to use an active temperature-controlled environment, where the radiation detection arrangement or one or more parts thereof may be arranged in a box, container, housing and the like for which the inner temperature may be actively controlled by using heating and/or cooling of the interior and at least one temperature sensor for temperature control.

Also, combinations of active and passive temperature-controlled environments may be used, wherein, for example, some parts of the radiation detection arrangement may be in an active temperature-controlled environment and other parts of the radiation detection arrangement are in a passive temperature-controlled environment.

Further, the present invention provides a method for measuring the effect of radiation on biological objects using a detection arrangement, wherein the method comprises the steps of:
   providing a detection layer comprising thermally activated delayed fluorescence TADF material, the thermally activated delayed fluorescence TADF material having an excitation frequency range and, exhibiting upon excitation with radiation in the excitation frequency range, a thermally activated delayed fluorescence TADF emission,
   detecting TADF emission from the detection layer by means of a radiation detector device, wherein
   the TADF material having a TADF emission without exposure to radiation and exhibiting a deviation in the TADF emission with exposure to radiation.

The method for measuring the effect of radiation on biological objects may further comprise the steps of:
   sub-dividing the detection layer into at least two channels, wherein each channel comprises the same TADF material or
   at least one channel, a plurality of channels or each channel comprises a different TADF material,
      selecting and/or mixing the components of the TADF material in order to create a suitable TADF material such that the properties of the resulting TADF material are physically, biologically and/or chemically substantially identical to the properties of the biological object and/or
      such that the activation energy of the resulting TADF material is substantially identical to the activation energy of biochemical reactions of the biological object;
   arranging the biological object in the vicinity of the radiation detection arrangement such that the biological object is being exposed to substantially the same external radiation as the radiation detection arrangement;
   wherein the method is further comprising:
   emitting excitation radiation in the excitation frequency range by means of an excitation radiation source device onto the detection layer and/or the one or more channel(s) in order to excite the one or more TADF material(s), wherein
   the excitation radiation causes TADF emission(s) of one or more of the TADF material(s), wherein
   each of the one or more TADF emission(s) having a brightness B that is depending on the composition of the TADF material and/or on the temperature T comprised in the one or more channels of the detection layer,
   a radiation detector device is communicatively coupled to a computing device for the detection of TADF emission from the detection layer and/or one or more channel(s);
   providing detection data from the radiation detector device to the computing device,
   computing the detection data from the radiation detector device to determine a TADF emission without exposure to external radiation and a deviation of the TADF emission with exposure to radiation,
   determining a brightness B of one or more TADF emission(s) in the detection layer and/or one or more channels(s),
   calculating a deviation of the brightness B of a TADF emission without exposure to external radiation and a brightness B of TADF emission with exposure to external radiation, determine and/or derive, on the basis of the deviation of the brightness B and/or on the basis of the temperature T of one or more TADF material(s) comprised in the detection layer or one or more channels, the effect of the external radiation on the biological object.

The method of the present invention may further comprise the steps of:

controlling the operation of the excitation radiation source device by means of a control device and emitting radiation, by operating the excitation radiation source device, in a constant emission mode and/or a variable/modifiable emission mode, comprising pulsed and/or periodical emission mode; and/or arranging an optical system between the detection layer and the radiation detector device for adjusting the TADF emission onto the radiation detector device; and/or at least one of:
  thermally calibrating the radiation detection arrangement for compensation of temperature related effects on the radiation detection device, and
  pressure calibrating the radiation detection arrangement for compensation of pressure related effects on the radiation detection device.

According to the method of the present invention, in an excitation phase, phase excitation radiation may be emitted onto the detection layer and/or one or more channel(s) in order to excite one or more TADF material(s) and, in a detection phase subsequent to the excitation phase, TADF emission(s) from the detection layer and/or one or more channel(s) may be detected.

In some examples, the excitation phase and the detection phase may, at least partially, overlap. For example:

the excitation phase and the detection phase may start at the same time and may take place for the same period of time;

the excitation phase and the detection phase may start at the same time, wherein the excitation phase ends, while the detection is phase is still ongoing and is continued for some further period of time;

the detection phase takes place for a period of time, during which at least two excitation phases take place one after another with a pause therebetween (i.e. period of time without excitation), wherein the at least excitation phases may have the same duration or different durations;

the excitation phase may start and, at some point of time when the excitation phase takes place, the detection phase may also start, wherein the excitation phase may end earlier or at the same time, or later than the detection phase.

In further examples, there may be a transition phase between the excitation phase and the detection phase, during which transition phase neither excitation nor detection takes place.

The method may further comprise the step of arranging an optical system between the detection layer and the radiation detector device for adjusting the TADF emission(s) onto the radiation detector device.

The method may further comprise the steps of:
providing a housing, having shielding properties to shield at least one of:
  electro-magnetic radiation,
  X-ray radiation,
  Ultraviolet radiation,
  Gamma radiation,
  Corpuscular radiation,
  alpha radiation,
  beta radiation,
  neutrons
  protons.

Further, the detection arrangement of the present invention is used for measuring the effect of radiation on biological objects.

SUMMARY OF THE DRAWINGS

In the description of embodiment further below, it is referred to the following drawings, which show.

DESCRIPTION OF EMBODIMENTS

Generally, features and functions referred to with respect to specific drawings and embodiments may also apply to other drawings and embodiments, unless explicitly noted otherwise.

Known conventional components, which are necessary for operation, (e.g. energy supply, cables, controlling devices, processing devices, storage devices, etc.), are neither shown nor described, but are nevertheless considered to be disclosed for the skilled person.

Figure 1:
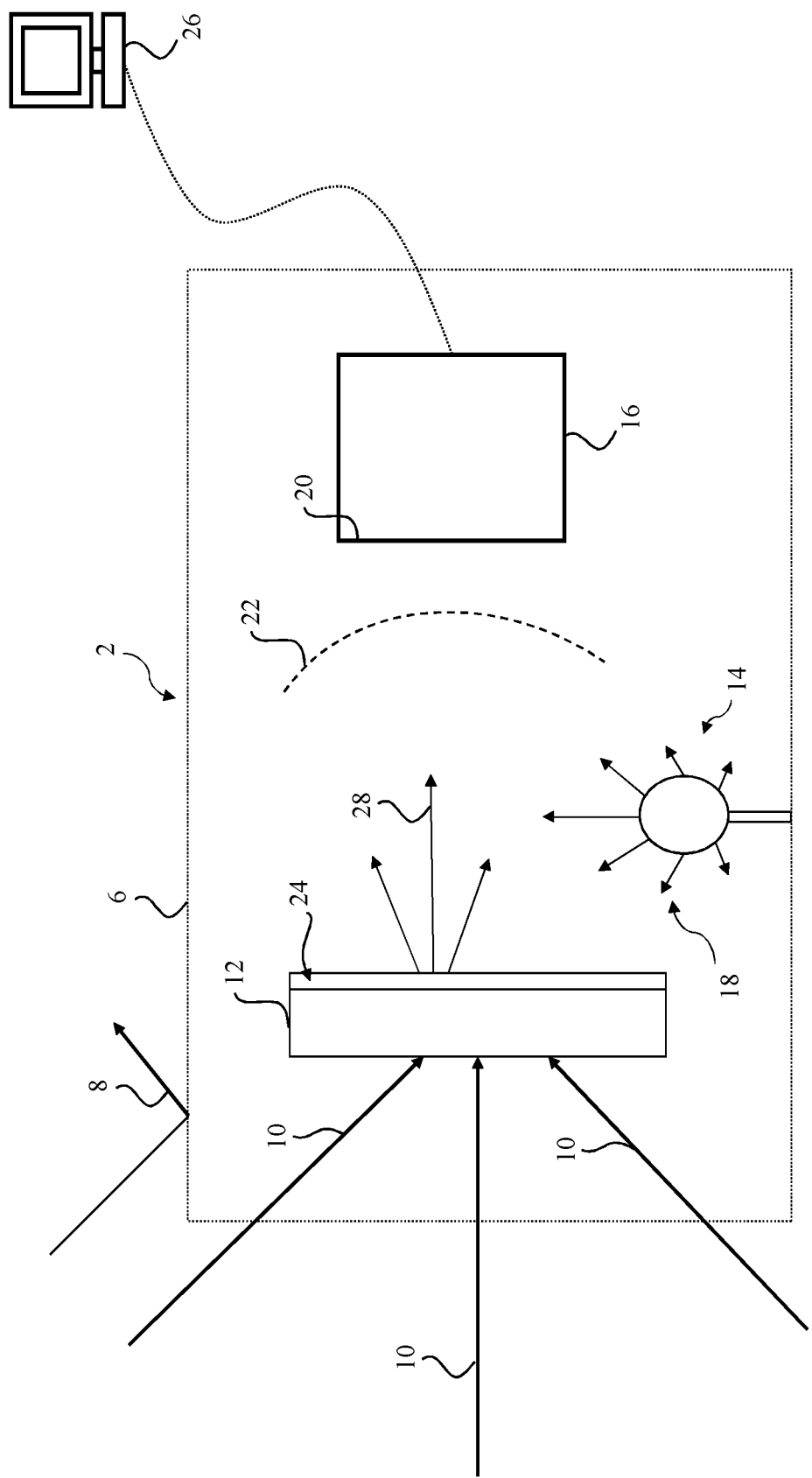
FIG. 1 a schematic illustration of a radiation detection arrangement for detection of external radiation, FIG. 1A a schematic illustration of a radiation detection arrangement and a biological object for the measurement of the effect of radiation on the biological object, FIG. 1B a schematic illustration of a radiation detection arrangement and a biological object for the measurement of the effect of radiation on the biological object using an optional housing for shielding, FIG. 1C a diagram illustrating an example calibration curve obtained from an experimental calibration of the radiation detection arrangement, FIG. 1D a diagram illustrating a health measurement of the biological object, FIG. 1E a schematic illustration of a detection layer of a radiation detection arrangement being sub-divided in channels, FIG. 1F a schematic illustration of a detection layer of a radiation detection arrangement being sub-divided in channels, FIG. 2 a schematic illustration of a further radiation detection arrangement for detection of external radiation, FIG. 3 a schematic illustration of a yet further radiation detection arrangement for detection of external radiation.

FIG. 1 schematically illustrates a radiation detection arrangement 2 for detection of external radiation 10. External radiation 10 refers to radiation impinging onto the radiation detection arrangement 2 and/or the radiation detection arrangement 2 is exposed to.

In the drawings, just three radiation beams along three directions (like from three sources) are illustrated. However, this is just for simplification. Rather, external radiation 10 may include more than those three radiation beams, namely a plurality thereof, as well as radiation showers, overlapping/crisscrossing beams and/or radiation fronts. Also, external radiation 10 may impinge from more than a direction, e.g. a plurality of different directions even opposing ones. The same applies for (shielded) radiation 8.

The radiation detection arrangement 2 may also comprise a housing 6. The housing 6 is illustrated in the drawings as a dashed line, indicating that the housing may be, depending on the experiment, omitted. In other words, providing the detection arrangement 2 with a housing 6 (e.g. in case some radiation 8 may be shielded) may not always be necessary. Accordingly, the detection arrangement 2, or the components thereof, do not necessarily have to be surrounded by the housing 6.

The housing 6, if used, may acts as shield against external radiation 8 that shall not be detected by the radiation detection arrangement 2, e.g. for a particular measurement. Such radiation is referred to as shieldable radiation 8. Examples for shieldable radiation 8 include one or more of the following: visible light, neutrons, electrons, protons, myons, cosmic radiation, electro-magnetic radiation, X-ray radiation, ultraviolet radiation, Gamma radiation, corpuscular radiation, alpha radiation, beta radiation, thermal radiation, thermal disturbances.

Contrary thereto, the housing 6 does not block, shield off or prohibit in any other way external radiation that may be measured. Such radiation is referred to a measurable radiation 10. Examples for measurable radiation 10 include one or more of the following: visible light, neutrons, electrons, protons, myons, cosmic radiation, electro-magnetic radiation, X-ray radiation, ultraviolet radiation, Gamma radiation, corpuscular radiation, alpha radiation, beta radiation, thermal radiation, thermal disturbances, neutrinos, neutralinos, WIMPS (Weakly interacting massive particles), high penetrating cosmic rays and particles, high penetrating radiation from nuclear reactors and nuclear sets or any other radiation and/or particles.

Generally, however, it is desired to measure the effect of the overall radiation, i.e. all radiation present and/or impinging/influencing the biological object. Thus, the housing 6 is, preferably, not used.

Figure 1A:
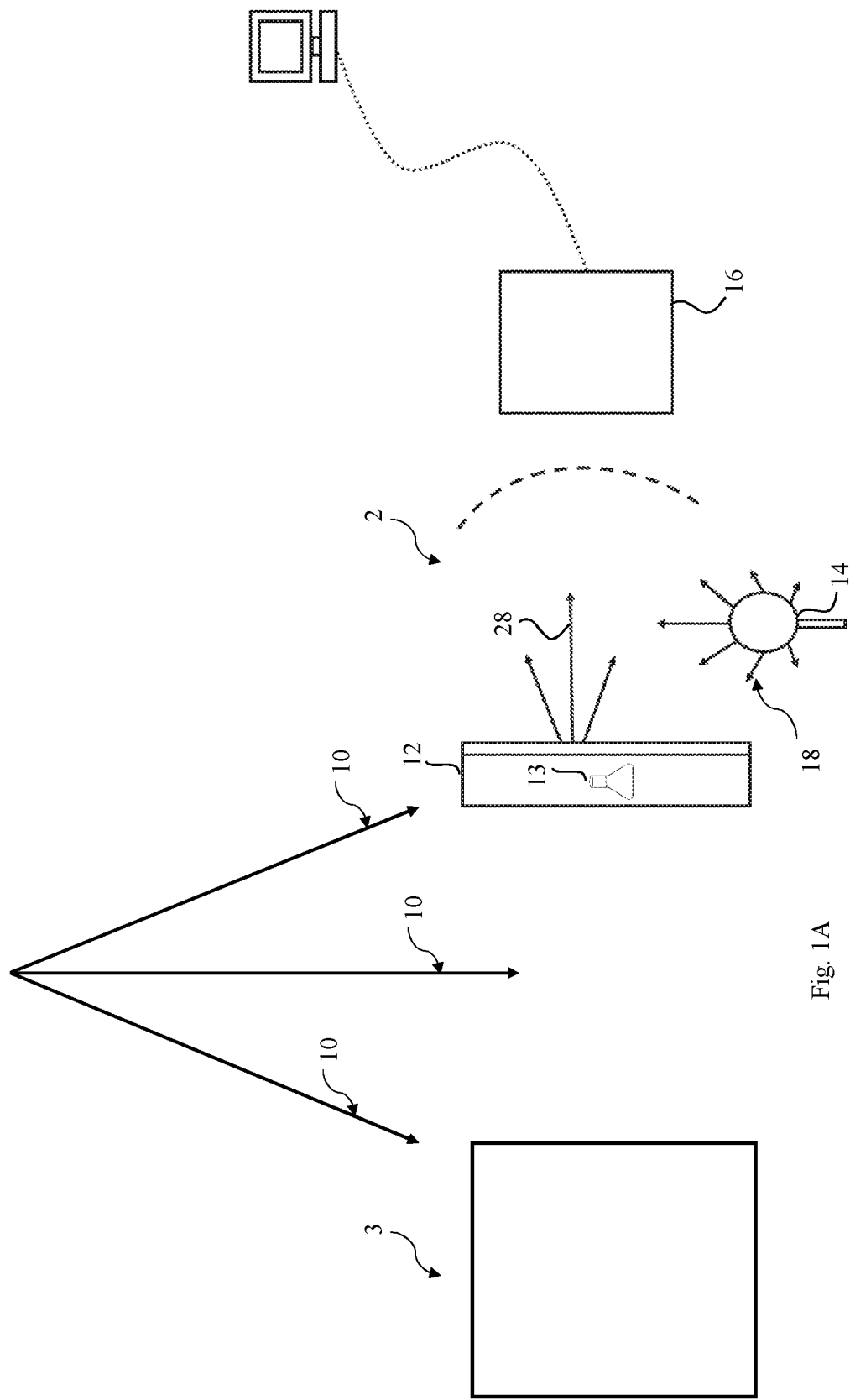

This is illustrated with a view on FIG. 1A, showing a biological object 3 along with the radiation detection arrangement 2 arranged substantially in the vicinity of thereof. In the example of FIG. 1A, however, a housing 6 is not used, such that the overall effect of all external radiation 10, i.e. all radiation 10 being present and/or impinging on both the biological object 3 and the radiation detection arrangement 2, is measured/detected.

As in the example of FIG. 1, the three radiation beams 10 are illustrated just for simplification, i.e. it may include more than those three radiation beams, namely a plurality thereof, as well as radiation showers, overlapping/crisscrossing beams and/or radiation fronts. Also, the three depicted radiation beams 10 do not have to come from the same source. Rather, there can be multiple sources and a variety of different radiations.

As can be seen by FIG. 1A, both the radiation detection arrangement 2 and the biological object 3 will be equally exposed to the same radiation 10 being present at e.g. a particular place, region or site. In other words, both are arranged in the vicinity of each other such that an equal radiation flux can be assumed.

Figure 1B:
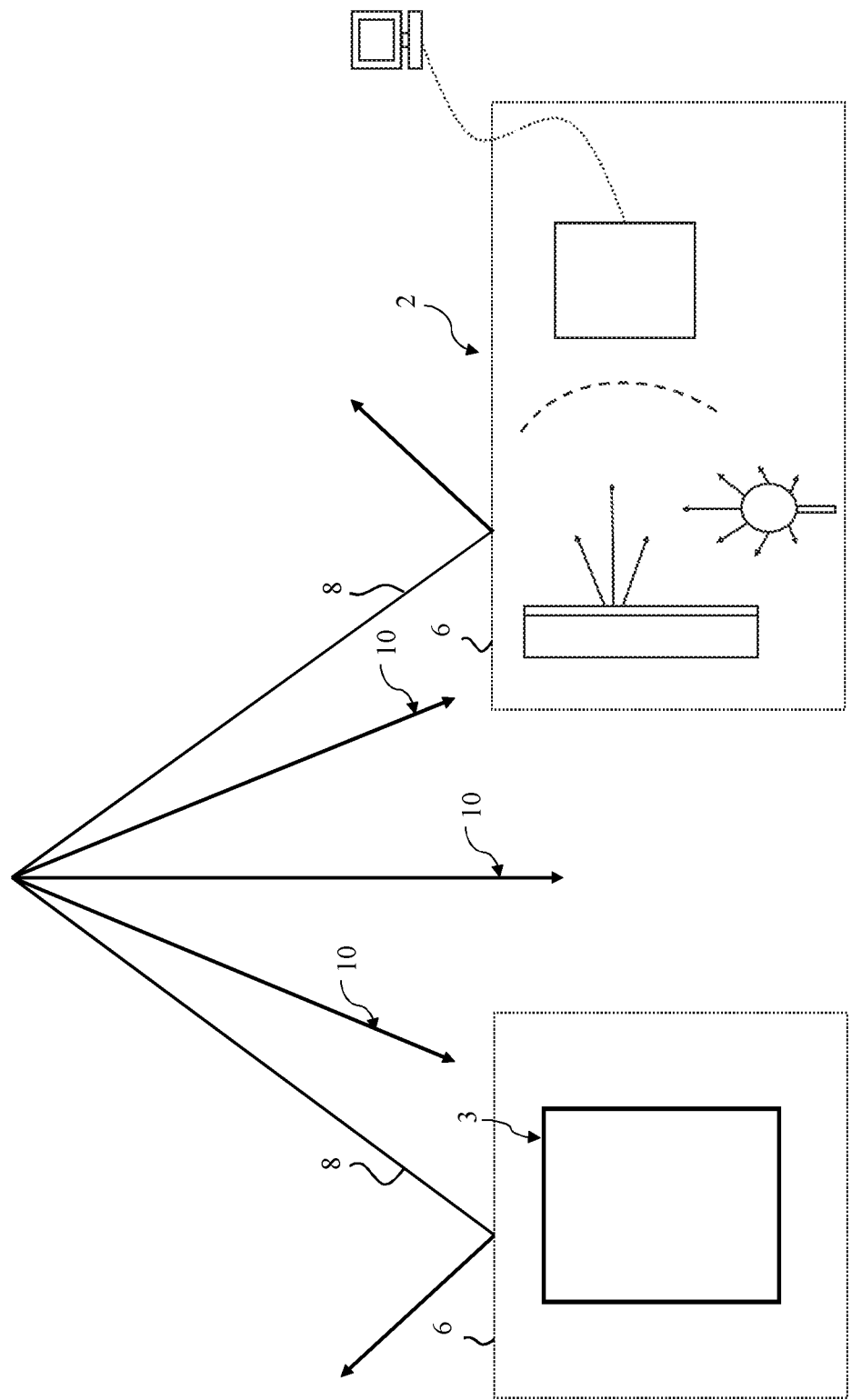

In other examples, however, as depicted in FIG. 1B, a housing 6 may be used, e.g. in cases where it is desired to shield particular radiation 8. As before, it should be noted that in such cases, both the radiation detection arrangement 2 and the biological object 3 may be shielded equally, i.e. the housing 6 used for the biological object 3 requires the same shielding properties as the housing 6 for the radiation detection arrangement. This ensures, that both the radiation detection arrangement 2 and the biological object 3 will be equally exposed to the same radiation.

In any case, however, the particles or radiation to be shielded depends on the particular radiation under investigation, i.e. both the detection arrangement 2 and the biological object 3 are selected to be exposed to. For example, it might be necessary to shield EM radiation in order to investigate the effect of gamma radiation on the biological object 3. Contrary thereto, i.e. in cases when the biological object 3 is not shielded or even cannot be shielded, the detection arrangement 2 will, similarly, also not be shielded.

In cases when a housing 6 is used, i.e. shielding is used, the housing 6 may be adapted to act as at least one of the following:
  optically non-transparent shield,
  thermal shield,
  electromagnetic shield,
  shield against at least one of UV radiation, gamma radiation, corpuscular radiation, X-rays, alpha radiation, beta radiation.

The material of the housing 6, if required, may comprise, for example, at least one of the following:
  metal (e.g. for optically non-transparent shielding),
  plastic (e.g. for optically non-transparent shielding),
  gas gap and/or low thermal conductivity polymers (e.g. for thermal shielding),
  multi layered construction including layers of different material, for example alternating layers of material having low and high thermal conductivity, like copper foil, (e.g. for thermal shielding),
  low thermal conductivity material, like polymer, (e.g. for thermal shielding),
  closed (e.g. complete and/or hermetic) grounded metal coating (e.g. Al, Cu) (e.g. for electromagnetic shielding)

UV/gamma/corpuscular/X-rays/alpha/beta shield:
  Aluminum (e.g. for shielding of at least one of UV radiation, gamma radiation, corpuscular radiation, X-rays, alpha radiation, beta radiation),
  glass (e.g. for shielding of at least one of UV radiation, gamma radiation, corpuscular radiation, X-rays, alpha radiation, beta radiation),
  textolite (e.g. for shielding of at least one of UV radiation, gamma radiation, corpuscular radiation, X-rays, alpha radiation, beta radiation),
  concrete (e.g. for shielding of at least one of UV radiation, gamma radiation, corpuscular radiation, X-rays, alpha radiation, beta radiation).

An exemplary housing may have walls comprising an Aluminum sheet/layer with a thickness of at least about 10 mm; one, two or three glass layers each having a thickness of at least about 2 mm; a textolite layer with a thickness of about 1 mm with an optional cooper foil at least at one side of the textolite layer.

The distance between the inner surface of the housing 6 and the detection layer 12 may be 0 mm (i.e. no distance) or, for example, in the range of at least about 30 mm.

Inside the housing 6, i.e. if a housing is required/used, the radiation detection arrangement 2 comprises a detection layer 12, which comprises at least a TADF material, i.e. material exhibiting thermally activated delayed fluorescence. The TADF material of the detection layer 12 has an excitation frequency range, where the TADF material, if being excited by radiation in the excitation frequency range, exhibits a thermally activated delayed fluorescence.

Also, inside the housing 6, i.e. if a housing is required/used, the radiation detection arrangement comprises an excitation radiation source 14 and a radiation detector device 16, e.g. a photo detector. If no housing 6 is required/used, the detection device illustrated in FIG. 1A may be used, i.e. the excitation radiation source 14 and the radiation detector device 16 may be placed substantially in the vicinity of the detection layer 12 and/or the emission surface 24.

The excitation radiation source device 14 is capable of providing radiation (at least) in the excitation frequency range of the TADF material. Such radiation is referred to as excitation radiation 18. The excitation radiation source device 14 can be controlled to provide continuous excitation radiation 18, i.e. to be operated in a constant emission mode. The excitation radiation source device 14 can be controlled to provide non-continuous excitation radiation 18, i.e. to be operated in a variable emission mode, to provide, for example, pulsed and/or periodical excitation radiation.

The excitation radiation source device 18 can comprise one or more excitation radiation sources, for example, one or more LEDs. The drawings show a single excitation radiation source device 18. However, two and more excitation radiation source devices arranged adjacent to each other or spaced from each other can be employed.

The radiation detector device 16 is capable of detecting (at least) radiation provided by the detection layer 12, particularly thermally activated delayed fluorescence from the TADF material in response to excitation by excitation radiation from the excitation radiation source device 18.

The radiation detector device 16 can comprise one or more radiation detectors, for example photo detectors being sensitive to a least fluorescence that the TADF material can emit.

Figure 2:
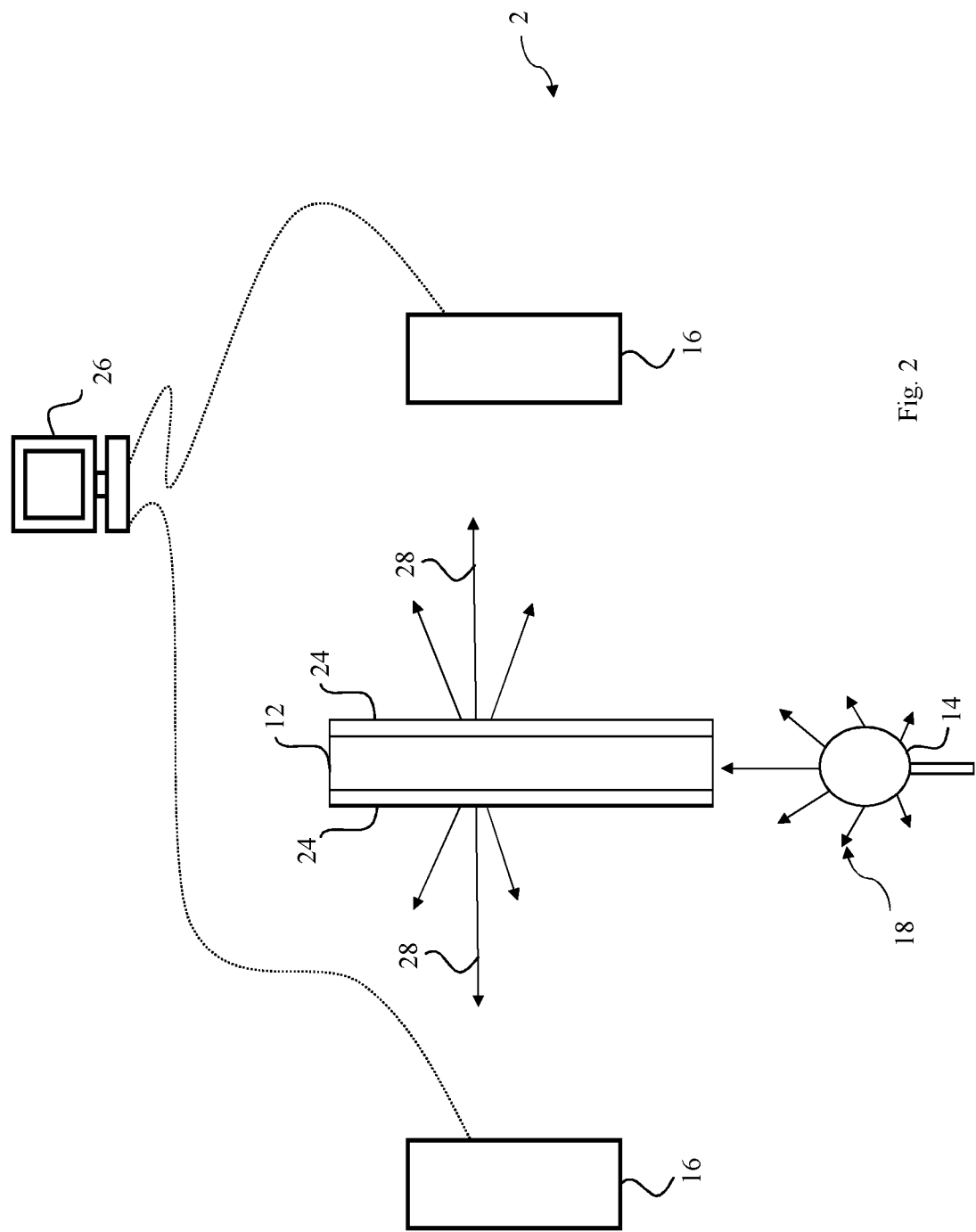
Figure 3:
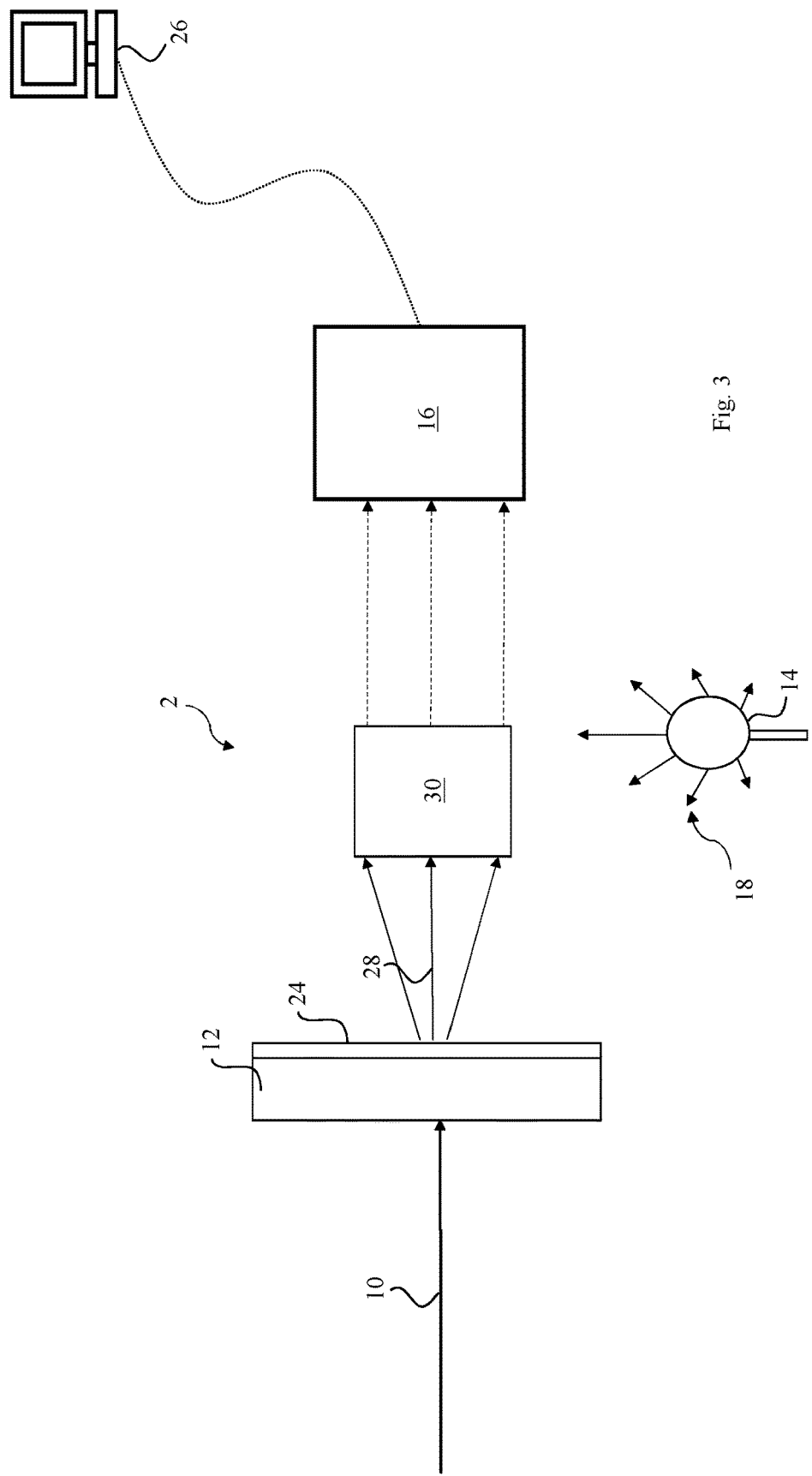

As illustrated in FIGS. 1 and 3, one radiation detector device 16 can be employed, while FIG. 2 illustrates an embodiment employing two radiation detector devices 16. However, more than two radiation detector devices 16 can be used, in order to, for example, detect radiation from the detection layer at different locations in the housing 6.

The radiation detector device 16 can have a planar detection surface 20, as illustrated in the drawing. However, radiation detector devices having a, for example, curved detection surface as indicated by the dashed curved detection surface 22 in FIG. 1.

The size and form of the detection surface can be designed such that it conforms the size and form of a detection layer's emission surface 24 from where detection layer radiation and, particularly, TADF fluorescence can be emitted. This allows capturing and detecting as much radiation from the detection layer as possible.

According to the illustrations of FIGS. 1 and 3, the detection layer 12 has a single emission surface 24, while the detection layer 12 of FIG. 2 has two emission surfaces 24.

The radiation detector device 16 is capable of outputting detection data indicating radiation detected by the radiation detector device 16.

In addition, or as alternative, an optical system can be arranged between the detection layer 12 and a radiation detector device 16, as explained further below with reference to FIG. 3.

The radiation detection arrangement 2 further includes computing device 26. The computing device 26 is communicatively coupled with the radiation detector device 16 to, at least, obtain detection data outputted from the radiation detector device 16. Further, the computing device 26 may be arranged to control the radiation detector device 16 and its operation, respectively.

The computing device 26 may be also communicatively coupled with the excitation radiation source device 14 to control the operation thereof.

A communicative coupling between the computing device 26 and another part of the radiation detection arrangement (e.g. the radiation detection device 16 and excitation radiation source device 14) may be wired and/or wireless.

The computing device 26 is adapted, e.g. in the form of respectively designed hardware and/or software, to compute detection data from the radiation detector device 26 in a manner to determine one or more emission resulting from radiation emitted by the detection layer and, particularly, from thermally activated delayed fluorescence from the TADF material.

If applicable, the computing device 26 may control the operation of the excitation radiation source device 14. For example, the excitation radiation source device 14 may be controlled such that it emits excitation radiation 18 synchronized with detection operation of the radiation detector device 26. In some examples, the following procedure may be used: The excitation radiation source device 14 may be operated to emit excitation radiation for a predefined first period of time (e.g. a phase of 1 ms).

Then, during a second predefined period of time (e.g. a phase of 1 ms) no excitation radiation is emitted and the radiation detector device 26 is not activated/operated to detect radiation from the detection layer 12 and, particularly thermally activated delayed fluorescence from the TADF material. This period of time and phase, respectively, allows transition processes to take place in, e.g., the TADF material and/or the hardware components of the arrangement.

After that, during a third predefined period of time (e.g. a phase of 3 ms) the radiation detector device 26 is activated/operated to detect radiation from the detection layer 12 and, particularly thermally activated delayed fluorescence from the TADF material.

This procedure can be referred to as radiation detection based on pre-excited TADF material, because in a first phase (also referred to an excitation phase) TADF material is excited by excitation radiation and in a second phase (also referred to a detection phase) TADF emission is detected/sensed on the basis of which measurable radiation can be detected. Preferably, as indicated above, there is an intermediate phase (also referred to as transition phase) between the excitation phase and the detection phase In other examples, the excitation radiation source device 14 may be operated to emit excitation radiation as pulses of the same or different level and/or with predefined time intervals of the same or varying length in between. Also, the excitation radiation source device 14 may be operated to emit constant excitation radiation (without periods without excitation radiation) of the same level or of at least two different levels (e.g. like a waveform or stepwise).

Generally, any type of one or more TADF material and combinations thereof may employed.

An exemplary TADF material used in experiments included an organic lumino for comprising a mixture of fluorescein Natrium and boric acid.

A possible mass ration of the components can be in the range of 1:100,000-1:500.

However, the composition of the TADF material is selected, synthesized and/or mixed and depends on the properties of the biological object. For example, the TADF material may be selected with respect to their activation energy and/or based on their response to biological reactions. In other words, one or more suitable TADF material(s) may be created such that their properties are as similar to the properties of a biological object as possible.

For example, the properties of the TADF material may be physically, biologically and/or chemically substantially as identical as possible to the properties of the biological object and/or the activation energy of the TADF material may as similar as possible to the activation energy of biochemical reactions of the biological object.

Further, various different TADF materials may be employed and used in the radiation detection arrangement.

The components can be mixed and heated to manufacture the exemplary TADF material, for example according to a heating profile. The mixed materials are, for example, heated up a maximal temperature in the range between 200° C. and 260° C. for at least 20 minutes under a pressure below 0.8 bar.

The heating may be performed in pre-molded forms to obtain TAFD material having a predefined shape. Also, after heating the material can be grounded and mixed with a carrier material (e.g. epoxy), after which the resulting material can be formed to get any desired shape (e.g. by applying onto a support surface).

According to the radiation detection device of FIG. 1, the TADF material of the detection layer 12 is excited by excitation radiation 18 from the excitation radiation source device 14, and in response thereto, emits thermally activated delayed fluorescence 28. The emitted thermally activated delayed fluorescence 28 impinges onto the radiation detector device 16, which generates respective detection data. The detection data generated by the radiation detector device 16 are computed by the computing device 26 to determine one or more emission resulting from thermally activated delayed fluorescence from the TADF material(s).

In general, this is also the case with the radiation detection devices of FIGS. 2 and 3.

Referring again to FIG. 1A, which illustrates the measurement of the effect of the overall radiation on the biological object 3 by the use of the detection arrangement 2, it should be noted that the TADF material 13 may be comprised in the detection layer 12 and/or one or more channel(s) 15 thereof.

The TADF material 13 in the detection layer 12 may be formed having desired and specially selected (and/or synthesized) component compositions. The TADF material will be excited by the excitation radiation 18 from the excitation radiation source device 14. In response thereto, the TADF material 13 emits thermally activated delayed fluorescence 28 that may be detected by the radiation detector device 16, e.g. by a photo detector.

The brightness B and/or amplitude of the emitted thermally activated delayed fluorescence 28 will depend on the TADF material(s) used, particularly, on their biological, physical and chemical properties. As mentioned before, the composition of the TADF material(s) 13 should be as close to the properties of the biological object 3 as possible, i.e. they should have almost identical physical, chemical and biological properties, e.g. structure, ratio, activation energy etc.

After excitation of the TADF material(s) 13 in the detection layer 12, it will emit light having e.g. a brightness, intensity and/or wavelength characteristic for the particular TADF material(s) used. This emission of light due to thermally activated delayed fluorescence may be referred to as glow or afterglow of the TADF material.

Knowledge about the brightness B, amplitude and/or intensity of the emission or afterglow may be used to determine and classify the emission(s) and also deviations/variations thereof. In the following, deviations/changes in emission(s) of TADF material(s) (i.e. deviations/changes in emission patterns or emission levels) will be referred to in the following as emission variations.

Before starting the measurements, the radiation detection arrangement 2 is calibrated and a nominal TADF emission may be determined. The nominal TADF emission may be used as a reference value (or indicator) for normal, i.e. optimal, conditions.

To this end, the radiation detection arrangement may be placed at a particular point or region in which (industrial or natural) sources of e.g. electromagnetic emission, alpha/beta/gamma radiation, extraterrestrial radiation due to solar flares at certain times or the like are absent, constant and/or at least at a minimum. In other words, only common background noise may be present. Those regions will be referred to in the following as calibration sites. While the detection arrangement 2 is being calibrated, influences of temperature or thermal effects may be controlled and/or compensated.

Calibrations sites may be found for example by the measurement of certain regions, sites or places using the measurements other (radiation) detectors and/or by waiting for certain times when extraterrestrial radiation, such as solar flares, are to be predicted to be at a minimum.

In the following, a possible calibration of the detection arrangement is discussed.

At a calibration site, the brightness B resulting from TADF emission may be determined/measured as a function of the Temperature T.

In other words, for any temperature value $t_{ci}$, one or more brightness values $B_{ci}$ of the TADF afterglow may be determined/measured, during calibration "c". The detection arrangement 2 may continue measuring brightness values for a certain time period for the temperature $t_{ci}$.

Then, another brightness value $B_{ci+1}$ may be measured for another temperature. This also allows to estimate/calculate a longtime mean TADF emission brightness for any temperature value. During calibration, however, the temperature value for which one or more brightness values of TADF emission(s) is measured, may be held constant.

Figure 1D:
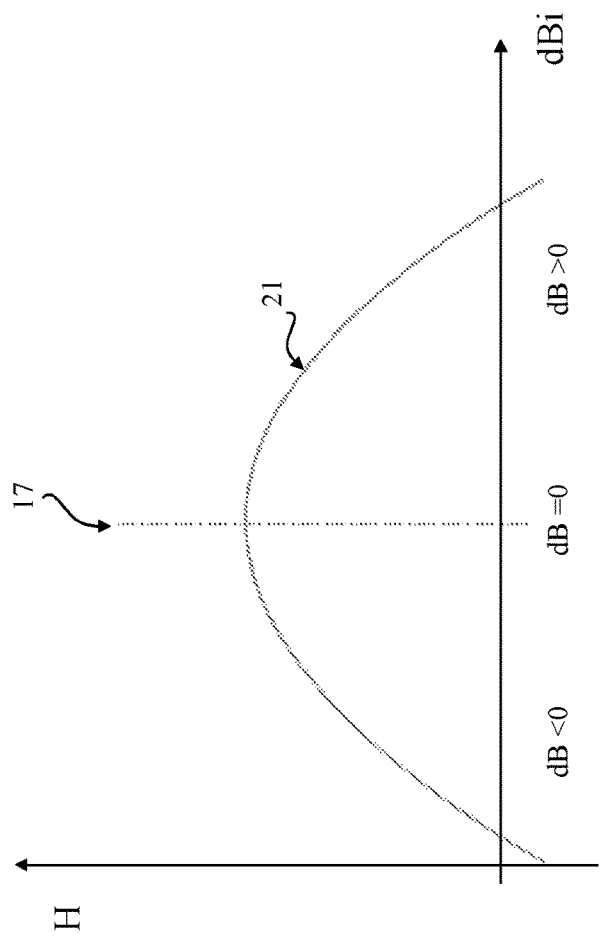
Figure 1C:
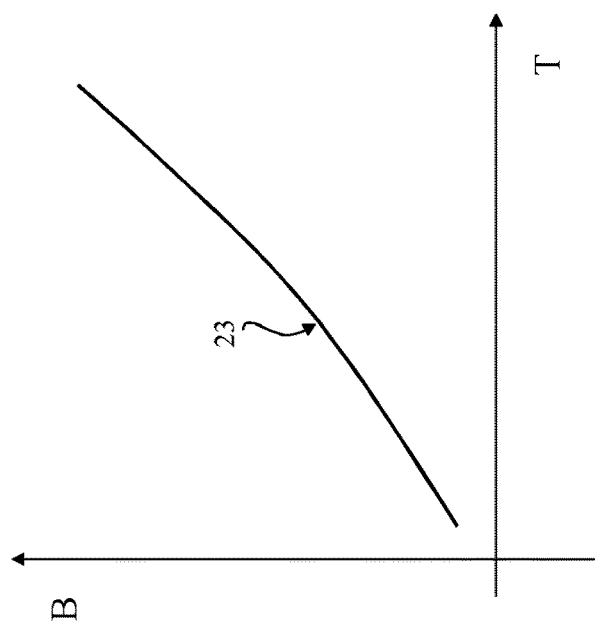

FIG. 1C is a diagram, showing a calibration curve $B_c(T)$ 23, i.e. the brightness B of TADF emission as a function of temperature T during an example calibration "c" at a calibration site.

Now, during actual measurements "m" of radiation of the detection arrangement 2, i.e. not at calibration sites and in case of external (measurable) radiation 10, values for the current temperature $t_{mi}$ and values for the brightness of the TADF afterglow $B_{mi}$ of the (one or more specific) TADF material(s) used may be determined/measured.

The determined/measured brightness values $B_{mi}$ of the measurement "m" may then be related to the determined/measured brightness values $B_{ci}$ of the calibration "c" of the radiation detection arrangement at a calibration site. To this end, the relation between the brightness values $B_{mi}$ and $B_{ci}$ may be described by a parameter $dB_i$ defined as follows:

$$dB_i = B_{mi}(t_{mi}) - B_{ci}(t_{ci}=t_{mi}), \quad (1)$$

wherein $B_{mi}$ may be the measured brightness value and $t_{mi}$ the temperature during the measurement. $B_{ci}(t_{ci}=t_{mi})$ is the brightness value $B_{ci}$ during the calibration "c" (see FIG. 1C) for the measured temperature $t_{mi}$.

Accordingly, the case $dB_i \neq 0$ may correspond to the case of external (measurable) radiation 10 being present and/or impinging on the radiation detection arrangement 2.

Furthermore, the radiation detection arrangement 2 may further continue to measure/detect brightness values $B_{mi}$ of TADF emission(s). Then, the measured values may be related and plotted via equation (1) resulting in Graph 21 illustrated in FIG. 1D. FIG. 1D shows the results of an example measurement using the radiation detection arrangement with prior calibration.

As set forth, graph 21 of FIG. 1D may regarded as the graphical representation of a further parameter H. In other words, another parameter H may be defined as the emission variation form the TADF emission(s).

As set forth, the parameter H may indicate an emission variation from the TADF emission(s) at a calibration site, i.e. the nominal (calibrated) TADF emission, to the TADF emission when external (measurable) radiation is present. Due to fact that the TADF material is selected to be as similar to the biological object as possible, it is possible to relate the parameter H to the biological object. Particularly, the parameter H may thus be considered to constitute a "health" measure for the biological object. Accordingly, the effect of radiation on the biological object may be measured, indicated and/or derived by/from the parameter H.

In other words, emission (brightness) variation(s) of one or more TADF material(s) may correspond to a health measurement H of the biological object.

The emission variation may be a variation/deviation in the brightness B of TADF material at a calibration site in comparison to the brightness B of TADF material when external (measurable) radiation is present. The emission radiation may be a function of the overall mean radiation present, i.e. both the radiation detection arrangement 2 and the biological object 3 are located in or exposed to.

Graph 21 of FIG. 1D illustrates possible emission variations, i.e. changes in brightness B of the afterglow of a TADF material. Three cases may be distinguished:

dB>0: Brightness of the TADF afterglow is higher than optimal/nominal TADF emission 17 (resulting in higher temperature T);

dB=0: Brightness of the TADF afterglow is zero, indicating optimal/nominal TADF emission 17;

dB<0: Brightness of the TADF afterglow is lower than optimal/nominal TADF emission (resulting in lower temperature T).

For example, a TADF emission (i.e. afterglow) being brighter than the nominal TADF emission 17 may be related to effects of higher temperature, for example inflammatory diseases, higher risk of mutations, excessive excitement etc., or hyper effects at different hierarchical levels, from intracellular reactions to overall functional systems including for example cardiovascular system, central nervous system, digestive.

On the other hand, a TADF emission (i.e. afterglow) being less bright than the nominal TADF emission 17 may be related to effects of lower temperature, for example depression, fatigue at different levels of biological organization, or hypo effects at different hierarchical levels, from intracellular reactions to overall functional systems including for example cardiovascular system, central nervous system, digestive.

FIG. 1E illustration of a detection layer 12 used in a radiation detection arrangement 2, being sub-divided in different channels 15 for detection of external radiation.

The number of channels 15 that the detection layer 12 will be sub-divided into generally depends on the biological object(s) under investigation. Multiple biological objects may be measured similarly. Further, it may be useful to sub-divide the detection layer 12 in at least two channels 12 or also in even more channels.

It is also possible, to only use one channel 15. In such cases, a single channel may correspond to the detection layer 12 disclosed e.g. in FIGS. 1, 1A, 1B, 2 and 3.

In the following, sub-diving of the detection layer 12 into channels may refer to form (sequential) channels 15 being e.g. being connected to each other such that the detection layer may be formed as, for example, a single (connected) element (i.e. as depicted in FIG. 1E).

Furthermore, sub-dividing the detection layer 12 into channels may refer to form channels 15 being independent from each other, such that the channels 15 may be formed as individual elements each having their own emission surface 24 as depicted in FIG. 1F. In this case, each individual channel may be considered to be just a (smaller) version of the detection layer 12 disclosed e.g. in FIGS. 1, 1A, 1B, 2 and 3.

It should be noted that the emission surface 24 is merely illustrated in the Figures for simplification and for characterizing where TADF emission may occur. Likewise, TADF emission may also occur in any other direction from the detection layer (and/or the channels), homogeneously, in multiple directions and, particularly, at any point, surface or position of the detection layer (and/or the channels). Thus, the emission surface 24 does not constitute a separate component of the radiation detection arrangement 2.

Furthermore, the channels 15 may have also a different number, may be overlapping, stapled, exchanged, (re)oriented, may be arranged in different layers or may have any desired form, structure, orientation, size, shape or design.

Also, the TADF material 13 within a certain channel 15 may have a material composition differing from the TADF material 13 within another channel 15. Furthermore, one channel 15, a variety of channels 15 or even all channels 15 may also comprise the same (or different) TADF material(s). Different combinations in number, composition, ratio and amount of the TADF material 13 and of the channels 15 will be considered to be disclosed for the skilled person.

As mentioned before, the TADF material 13 as well as the channels 15 used depend on the biological object(s), for example, on biological, chemical and/or physical properties.

In any case however, the channels 15 and/or the TADF material(s) to be used should be selected/mixed/synthesized to be, biologically, physically and/or chemically as identical to the biological object as possible.

However, in the radiation detection device of FIG. 2, two radiation detector devices 16 are used to detect thermally activated delayed fluorescence 28 emitted by the TADF material of the detection layer 12. The detection data respectively generated by the radiation detector devices 16 are computed by the computing device 26 to determine one or more emission patterns resulting from thermally activated delayed fluorescence from the TADF material. Since detection data from two radiation detector devices 16 are available, the detection data from the different radiation detector devices 16 can be used to compare the one or more emission patterns on one of radiation detector devices 16 with the one or more emission patterns of the other radiation detector device 16.

For example, two and more radiation detector devices 16 can be used for a correlated detection of measurable radiation 10, wherein, e.g., only synchronized detection data from different radiation detector devices 16. Synchronization may include to operate the radiation detection devices 16 such that their respective detection data are provided at the same time or processed such that detection data generated at the same time and/or in the same time period are processed together. In addition, or as alternative, synchronization may include to use together detection data being generated at/in corresponding areas of the respective detection surfaces of the radiation detection devices 16. In addition, or as alternative, synchronization may include using detection data being indicative of TADF emission coming from different parts/surfaces of the detection layer 12 and TADF material, respectively, in order to, for example, detect TADF emission from opposing detection layer's surfaces as illustrated in FIG. 2.

As further example, two and more radiation detector devices 16 can be used to distinguish different types of measurable radiation 10, wherein, e.g., differences between detection data from different radiation detector devices 16 are calculated.

In the radiation detection device of FIG. 3, an optical system 30 is used to collect and/or focus thermally activated delayed fluorescence from the TADF material onto the radiation detector device 16, in order to, for example, avoid "loosing" such radiation from being captured by the radiation detector device.

As known, in response to excitation radiation, generally TADF material exhibits two effects, namely TAFD emission and phosphorescence emission. While phosphorescence emission results from an inter system crossing (ISC) transition, i.e. a transition from the S1 state to the T1 state, TADF emission results from a reverser ISC transition, i.e. a transition from the T1 state to the S1 state.

However, experiments have demonstrated that phosphorescence emission does not show a reaction to external radiation and measurable radiation, respectively; at least the reaction has not impact on the radiation detection based on TAFD emission. Particularly, external/measurable radiation does not affect phosphorescence emission of TADF material in the way as TADF emission. Rather, the phosphorescence emission pattern remains essential the same. Therefore, phosphorescence emission impinging on the radiation detection device 16 can be considered as essentially constant background light.

Data outputted by the radiation detection device 16 in response to received phosphorescence emission can be compared with background noise and treated in the same way. For example, overall data output from the radiation detection device 16 may be filtered to remove phosphorescence emission related data in order to obtain, as effective radiation detection device output, detection data being indicative of TADF emission.

In general, TADF material is temperature sensitive and, as a result, has temperature dependent TADF emission. Therefore, a thermal calibration method may be used to compensate temperature related effect.

For example, the whole radiation detection arrangement 2 may be set up in a thermally controlled thermal chamber, in which the temperature is controlled to change from a low/minimum level to a high/maximum level, preferably with constant speed. The temperature may be changed so slow that, inside the thermal chamber, a quasi thermal equilibrium is achieved. For example, the temperature change may be such that the time constant of the thermal calibration method time constants of the thermal calibration method are smaller than dynamics of the thermal chamber of the thermal calibration setting. For example, in some cases the time constant of the thermal calibration method can be in the range of about two seconds and measuring time constant of the thermal calibration setting can be in the range of about two minutes. As further example, the thermal dynamics of the thermal calibration setting can be a thermal change in the range of about 20° C. in about one hour.

The above temperature change process may carried out once or may be repeated for two or more different temperature change profiles (e.g. different constant speeds, stepwise including using different step sizes). Experiments have shown that one or more temperature change processes lasting about five to seven hours provide a good basis for thermal calibration.

During thermal calibration, the radiation detection arrangement 2 may be operated normally, for example, so that the TADF material is excited by excitation radiation and TADF emission is detected by the radiation detector device 16.

During the temperature change process(es), temperature and changes thereof of at least one of the detection layer 12 and/or the channels, the TADF material, the excitation radiation source device 14 (and/or components thereof), the radiation detection device 16, the detection surface (e.g. detection surface 20 or 22), the detection layer's surface, the optical system 30, the housing 6 and electrical and/or electronic components (e.g. cables, amplifiers, signal conditioners, ADCs etc.) in the housing and/or in the thermal chamber are measured. This may be accomplished by one or more temperature sensors respectively arranged in/on the housing and/or the thermal chamber.

The thusly measured temperatures and changes thereof (e.g. in form of respective time series) and, particularly, information on the TADF material temperature and changes thereof, can be used to determine information (e.g. in form of regression curves) indicative of the temperature dependency of the radiation detection arrangement 2 and parts thereof, for example data output by the radiation detector device 16 and/or data received by the computing device 26.

Such information may be used to compensate temperature dependent effects in radiation detection by the radiation detection device 2.

In this context, it is noted that it can be assumed that generally there is no correlation between, on the one hand, external radiation 4 reaching the radiation detection arrangement 2 and measurable radiation 10 reaching the detection layer 12 and, on the other hand, temperature changes affecting the radiation detection arrangement 2. Nevertheless, it is preferred to not carry out calibration during unusual cosmic events, like full/new moon, solar flares and/or storms, Midheaven (Milky Way at MC point), for avoiding impacts thereof onto calibration.

Above, the present invention has been described with reference to detection of radiation space born and from outer space, respectively, as well as of radiation from radioactive material. However, the present invention is not limited to such applications, but can be used to detect any radiation of (very) low intensity and application using such information.

This patent arises from a U.S. Patent Application that claims the benefit of, and priority to, European Patent Application EP 17 202 468.9, filed Nov. 19, 2017. European Patent Application EP 17 202 468.9 is hereby incorporated herein in its entirety.

| | Reference numeral list |
|---|---|
| 2 | Radiation detection arrangement |
| 3 | Biological object |
| 4 | External radiation |
| 6 | Housing |
| 8 | Shieldable radiation |
| 10 | Measurable radiation |
| 12 | Detection layer |
| 13 | TADF material |
| 14 | Excitation radiation source device |
| 15 | Channel |
| 16 | Radiation detector device |
| 17 | Nominal value |
| 18 | Excitation radiation |

-continued

| Reference numeral list | |
|---|---|
| 20 | Planar detection surface |
| 21 | Graphical representation of "health" parameter H |
| 22 | Curved detection surface |
| 23 | Calibration curve |
| 24 | Detection layer's surface |
| 26 | Computing device |
| 28 | Thermally activated delayed fluorescence |
| 30 | Optical system |

The invention claimed is:

1. Detection arrangement for measuring the effect of radiation on biological objects, the arrangement comprising:
a detection layer comprising thermally activated delayed fluorescence TADF material, the thermally activated delayed fluorescence TADF material having an excitation frequency range and, exhibiting upon excitation with radiation in the excitation frequency range, a thermally activated delayed fluorescence TADF emission, wherein
the TADF material having a TADF emission without exposure to external radiation and exhibiting a deviation in the TADF emission with exposure to external radiation.

2. Detection arrangement for measuring the effect of radiation on biological objects, according to claim 1,
wherein the detection layer is sub-divided into at least two channels,
wherein each channel comprises the same TADF material or
at least one channel, a plurality of channels or each channel comprises a different TADF material,
wherein the components of the TADF material are selected and/or mixed in order to create a suitable TADF material
such that the properties of the resulting TADF material are physically, biologically and/or chemically substantially identical to the properties of the biological object and/or
such that the activation energy of the resulting TADF material is substantially identical to the activation energy of biochemical reactions of the biological object; wherein
the biological object is arranged in the vicinity of the radiation detection arrangement and
is being exposed to substantially the same external radiation as the radiation detection arrangement;
wherein the detection arrangement is further comprising:
a computing device,
an excitation radiation source device adapted to emit excitation radiation in the excitation frequency range, wherein
the excitation radiation causes TADF emission(s) of one or more of the TADF material(s), wherein
each of the one or more TADF emission(s) having a brightness B that is depending on the composition of the TADF material and/or on the temperature T comprised in the one or more channels of the detection layer,
a radiation detector device communicatively coupled with the computing device, the radiation detector device being adapted to detect TADF emission from the one or more channels and provide respective detection data to the computing device,
wherein the computing device is being adapted to:
compute detection data from the radiation detector device to determine a TADF emission without exposure to external radiation and a deviation of the TADF emission with exposure to radiation,
determine a brightness B of one or more TADF emission(s) in the detection layer and/or one or more channels(s) and
calculate a deviation of the brightness B of a TADF emission without exposure to external radiation and a brightness B of TADF emission with exposure to external radiation,
determine and/or derive, on the basis of the deviation of the brightness B and/or the temperature T of one or more TADF material(s) comprised in the detection layer and/or one or more channels, the effect of the external radiation on the biological object.

3. The detection arrangement of claim 1, wherein the detection layer and/or one or more channel(s) is at least one of
planar,
provided in a coating material,
shaped as a part of a sphere,
shaped as a hollow or solid sphere,
shaped as a polyhedron.

4. The detection arrangement of claim 2, wherein the radiation detector device comprises at least one of
a photo detector,
a discrete radiation detector,
a radiation detector array including at least two detector elements,
electro-optical transducer,
image intensifier tube,
vacuum tube,
CMOS chip
a CCD chip.

5. The detection arrangement of claim 1, comprising
at least two radiation detector devices, wherein the detection layer and/or one or more channel(s) are arranged between the at least two radiation detector devices;
a control device for controlling the operation of the excitation radiation source device, wherein the control device is adapted to operate the excitation radiation source device in a constant emission mode and/or a variable/modifiable emission mode, comprising pulsed and/or periodical emission mode, wherein, preferably,
the computing device is able to compute detection data from the radiation detector device during and/or following radiation emission from the excitation radiation source device and/or
an optical system being arranged between the detection layer and/or one or more channel(s) and one or more of the radiation detector device.

6. The detection arrangement of claim 1, comprising a housing accommodating the components of the detection arrangement.

7. The detection arrangement of claim 1, wherein the housing has shielding properties for shielding of at least one of:
electro-magnetic radiation;
X-ray radiation;
ultraviolet radiation;
Gamma radiation;
corpuscular radiation, comprising alpha radiation, beta radiation, neutrons and/or protons.

8. The detection arrangement of claim 1,
comprising at least one temperature sensing device for sensing temperature of at least one of
the detection layer,
the one or more channels,
one or more TADF material(s),
the excitation radiation source device,
the radiation detector device,
the housing,
the optical system,
the computing device, and/or
wherein the detection arrangement or at least one part thereof is arranged in a temperature-controlled environment.

9. Method for measuring the effect of radiation on biological objects using a detection arrangement, comprising:
providing a detection layer comprising thermally activated delayed fluorescence TADF material, the thermally activated delayed fluorescence TADF material having an excitation frequency range and, exhibiting upon excitation with radiation in the excitation frequency range, a thermally activated delayed fluorescence TADF emission,
detecting TADF emission from the detection layer by means of a radiation detector device, wherein
the TADF material having a TADF emission without exposure to radiation and exhibiting a deviation in the TADF emission with exposure to radiation.

10. Method for measuring the effect of radiation on biological objects according to claim 9, comprising:
sub-dividing the detection layer into at least two channels, wherein each channel comprises the same TADF material or at least one channel, a plurality of channels or each channel comprises a different TADF material,
selecting and/or mixing the components of the TADF material in order to create a suitable TADF material
such that the properties of the resulting TADF material are physically, biologically and/or chemically substantially identical to the properties of the biological object and/or
such that the activation energy of the resulting TADF material is substantially identical to the activation energy of biochemical reactions of the biological object;
arranging the biological object in the vicinity of the radiation detection arrangement such that the biological object is being exposed to substantially the same external radiation as the radiation detection arrangement;
wherein the method is further comprising:
emitting excitation radiation in the excitation frequency range by means of an excitation radiation source device onto the detection layer and/or the one or more channel(s) in order to excite the one or more TADF material(s), wherein
the excitation radiation causes TADF emission(s) of one or more of the TADF material(s), wherein
each of the one or more TADF emission(s) having a brightness B that is depending on the composition of the TADF material and/or on the temperature T comprised in the one or more channels of the detection layer,
a radiation detector device is communicatively coupled to a computing device for the detection of TADF emission from the detection layer and/or one or more channel(s);
providing detection data from the radiation detector device to the computing device,
computing the detection data from the radiation detector device to determine a TADF emission without exposure to external radiation and a deviation of the TADF emission with exposure to radiation,
determining a brightness B of one or more TADF emission(s) in the detection layer and/or one or more channels(s),
calculating a deviation of the brightness B of a TADF emission without exposure to external radiation and a brightness B of TADF emission with exposure to external radiation,
determine and/or derive, on the basis of the deviation of the brightness B and/or on the basis of the temperature T of one or more TADF material(s) comprised in the detection layer or one or more channels, the effect of the external radiation on the biological object.

11. Method according to claim 9, further comprising:
controlling the operation of the excitation radiation source device by means of a control device and
emitting radiation, by operating the excitation radiation source device, in a constant emission mode and/or a variable/modifiable emission mode, comprising pulsed and/or periodical emission mode; and/or
arranging an optical system between the detection layer and the radiation detector device for adjusting the TADF emission onto the radiation detector device; and/or
at least one of:
thermally calibrating the radiation detection arrangement for compensation of temperature related effects on the radiation detection device, and
pressure calibrating the radiation detection arrangement for compensation of pressure related effects on the radiation detection device.

12. Method according to claim 10, wherein, in an excitation phase, phase excitation radiation is emitted onto the detection layer in order to excite the TADF material and, in a detection phase subsequent to the excitation phase, TADF emission from the detection layer and/or one or more channel(s) is detected, wherein the excitation phase and the detection phase may overlap or there may be a transition phase between the excitation phase and the detection phase, during which transition phase neither excitation nor detection takes place.

13. Method according to claim 9, further comprising:
providing a housing, having shielding properties to shield at least one of:
electro-magnetic radiation,
X-ray radiation,
Ultraviolet radiation,
Gamma radiation,
Corpuscular radiation,
alpha radiation,
beta radiation,
neutrons
protons.

14. Use of a detection arrangement according to claim 1 for measuring the effect of radiation on biological objects.

* * * * *